(12) United States Patent
Chernosky et al.

(10) Patent No.: US 9,579,141 B2
(45) Date of Patent: Feb. 28, 2017

(54) ORTHOPEDIC DEVICE HOLDER AND RELATED SYSTEM AND METHOD

(71) Applicant: Zimmer, Inc., Warsaw, IN (US)

(72) Inventors: John Chernosky, Brick, NJ (US); Ray Zubok, Midland Park, NJ (US); Timothy A. Hoeman, Morris Plains, NJ (US); Imants Liepins, Asbury, NJ (US)

(73) Assignee: Zimmer, Inc., Warsaw, IN (US)

( * ) Notice: Subject to any disclaimer, the term of this patent is extended or adjusted under 35 U.S.C. 154(b) by 414 days.

(21) Appl. No.: 14/175,061

(22) Filed: Feb. 7, 2014

(65) Prior Publication Data

US 2014/0276842 A1    Sep. 18, 2014

Related U.S. Application Data

(60) Provisional application No. 61/782,352, filed on Mar. 14, 2013, provisional application No. 61/825,653, filed on May 21, 2013.

(51) Int. Cl.
| | |
|---|---|
| *A61B 17/92* | (2006.01) |
| *A61F 2/46* | (2006.01) |
| *A61B 17/16* | (2006.01) |
| *A61B 17/00* | (2006.01) |

(52) U.S. Cl.
CPC .......... *A61B 17/92* (2013.01); *A61B 17/1604* (2013.01); *A61F 2/4603* (2013.01); *A61B 2017/00477* (2013.01); *A61B 2017/922* (2013.01)

(58) Field of Classification Search
CPC ....... A61B 17/92; A61F 2/4603; A61F 2/4609
See application file for complete search history.

(56) References Cited

U.S. PATENT DOCUMENTS

| | | | | |
|---|---|---|---|---|
| 319,095 | A | * 6/1885 | Joel ........................ | G04D 3/045 279/2.12 |
| 4,990,149 | A | 2/1991 | Fallin | |
| 5,057,112 | A | 10/1991 | Sherman et al. | |
| 5,089,003 | A | 2/1992 | Fallin et al. | |
| 5,169,399 | A | * 12/1992 | Ryland ................. | A61F 2/4609 606/91 |

(Continued)

*Primary Examiner* — David Bates
(74) *Attorney, Agent, or Firm* — Schwegman Lundberg & Woessner, P.A.

(57) ABSTRACT

An orthopedic device holder and related system and method are disclosed. The orthopedic device holder can include a body member, a cannulated plunger, and a resilient member. The body member can include a longitudinal main body and an extension portion. The cannulated plunger can be slidably mounted inside the body member and movable between a first position and a second position. The plunger can be configured such that in the second position, a plunger distal end extends past a main body distal end, and in the first position, the plunger distal end assumes a more proximal position. The resilient member can be positioned adjacent a plunger proximal end and can be configured to urge the plunger towards the second position. The extension portion of the body member can project distally from the main body distal end and can include a locking member, which can be configured to fit into a mating recess of an orthopedic device.

15 Claims, 8 Drawing Sheets

(56) References Cited

U.S. PATENT DOCUMENTS

| | | | |
|---|---|---|---|
| 5,443,471 A | | 8/1995 | Swajger |
| 5,484,132 A | * | 1/1996 | George ................ A63B 29/024 |
| | | | 248/231.9 |
| 5,499,986 A | | 3/1996 | Dimarco |
| 5,540,697 A | * | 7/1996 | Rehmann .............. A61F 2/4609 |
| | | | 294/95 |
| 5,569,256 A | | 10/1996 | Vaughn et al. |
| 5,683,399 A | * | 11/1997 | Jones ........................ A61F 2/34 |
| | | | 606/91 |
| 6,565,508 B2 | | 5/2003 | Scirica et al. |
| 6,817,862 B2 | | 11/2004 | Hickok |
| 7,235,082 B2 | * | 6/2007 | Bartish ................ A61F 2/4465 |
| | | | 606/99 |
| 7,670,296 B2 | | 3/2010 | Molnar et al. |
| 7,976,545 B2 | | 7/2011 | Hershberger et al. |
| 7,988,692 B2 | | 8/2011 | Lechot |
| 8,500,744 B2 | * | 8/2013 | Wozencroft .......... A61F 2/4609 |
| | | | 606/91 |
| 9,439,778 B2 | * | 9/2016 | Biedermann ......... A61F 2/4465 |
| 2003/0149438 A1 | * | 8/2003 | Nichols ................ A61B 17/025 |
| | | | 606/99 |
| 2007/0093897 A1 | * | 4/2007 | Gerbec ................ A61F 2/4465 |
| | | | 623/17.11 |
| 2008/0269768 A1 | * | 10/2008 | Schwager ............. B25B 23/108 |
| | | | 606/104 |
| 2011/0306984 A1 | * | 12/2011 | Sasing ............... A61B 17/8888 |
| | | | 606/104 |
| 2012/0150301 A1 | | 6/2012 | Gamache et al. |

\* cited by examiner

ORTHOPEDIC DEVICE HOLDER AND RELATED SYSTEM AND METHOD

CLAIM OF PRIORITY

This application claims the benefit of U.S. Provisional Patent Application Ser. No. 61/782,352, filed on Mar. 14, 2013, and also claims the benefit of U.S. Provisional Patent Application Ser. No. 61/825,653, filed on May 21, 2013, the benefit of priority of each of which is claimed hereby, and each of which are incorporated by reference herein in its entirety.

TECHNICAL FIELD

This patent document pertains generally, but not by way of limitation, to tool or device holders including a quick connection and release configuration.

BACKGROUND

It can be advantageous in many fields of endeavor for tool and device connection and release configurations to be quick and easy in nature. In the surgical field, for example, quick tool and device connection and release configurations can reduce surgery time and improve surgical results.

OVERVIEW

The present inventors recognize, among other things, that a quick connection and release configuration for a tool or device can be beneficial. In some procedures, a tool or device can require cannula access, which can make such a quick connection and release configuration complicated. The present invention provides an orthopedic device holder that can include a cannulated structure and provide a quick connection and release configuration for a tool or device. The device holder can have wide applications outside of the orthopedic field as well, particularly in applications where a quick connection and release configuration can be beneficial. In the orthopedic field, the device holder can be readily used with broaching sets, which can include multiple broaches of differing shapes or sizes. A proximal end of the orthopedic device holder can be configured for impact blows relating to broaching, chiseling, or compaction, for example.

To further illustrate the orthopedic device holder, system, and method disclosed herein, a non-limiting list of examples is provided here:

In Example 1, an orthopedic device holder can comprise a body member, a cannulated plunger, and a resilient member. The body member can include a longitudinal main body and an extension portion. The longitudinal main body can extend from a main body proximal end to a main body distal end and can include an interior surface and an exterior surface. The cannulated plunger can extend from a plunger proximal end to a plunger distal end and can be slidably mounted adjacent the interior surface of the main body. The cannulated plunger can be movable between a first position and a second position. In the second position, the plunger distal end extends past the main body distal end, and in the first position, the plunger distal end assumes a more proximal position. The resilient member can be positioned adjacent the plunger proximal end and can be configured to urge the plunger towards the second position. The extension portion can project distally from the main body distal end and can include a locking member. The locking member can have a first outer radial size and an arm member having a second outer radial size, which is less than the first outer radial size.

In Example 2, the device holder of Example 1 can optionally be configured such that the locking member is configured to fit into a mating recess of an orthopedic device.

In Example 3, the device holder of Example 2 can optionally be configured such that a combination including the locking member and the plunger, when in the second position, is configured to securely hold the orthopedic device.

In Example 4, the device holder of any one or any combination of Examples 2 or 3 can optionally be configured such that at least a portion of the main body distal end includes an engagement surface substantially perpendicular to an extension of the longitudinal main body.

In Example 5, the device holder of Example 4 can optionally be configured such that the engagement surface comprises a locating member, disposed on an opposite side of the main body distal end from the projecting extension portion, configured to mate with a corresponding locating member disposed on the orthopedic device.

In Example 6, the device holder of any one or any combination of Examples 1-5 can optionally further comprise a retraction handle, coupled to the plunger proximal end, configured to move the plunger from the second position toward the first position.

In Example 7, the device holder of Example 6 can optionally be configured such that the longitudinal main body includes one or more slots configured to guide movement of the retraction handle between a second position, associated with the second position of the plunger, and a first position, associated with the first position of the plunger.

In Example 8, the device holder of any one or any combination of Examples 1-7 can optionally be configured such that the main body proximal end includes an impaction surface having a larger cross-sectional area than a cross-sectional area of the main body distal end.

In Example 9, the device holder of Example 8 can optionally be configured to further comprise a resilient member retainer coupled to a lumen within the main body proximal end.

In Example 10, the device holder of any one or any combination of Examples 1-9 can optionally be configured such that the body member and the cannulated plunger collectively define a lumen extending from the main body proximal end, through the cannulated plunger, and through the main body distal end.

In Example 11, the device holder of Example 10 can optionally be configured such that a first portion of the lumen is formed by an interior surface of the main body proximal end, a second portion of the lumen is formed by an interior surface of the plunger, and a third portion of the lumen is formed, in part, by an interior surface of the extension portion.

In Example 12, the device holder of any one or any combination of Examples 1-11 can optionally be configured such that the first outer radial size of the locking member is substantially equal to an outer radial size of the longitudinal main body.

In Example 13, the device holder of any one or any combination of Examples 1-12 can optionally be configured such that the locking member includes a semi-circular dovetail configuration.

In Example 14, an orthopedic system can comprise the orthopedic device holder of any one or any combination of Examples 1-13 and at least one orthopedic device including a recess sized and shaped to receive portions of the locking member.

In Example 15, the orthopedic system of Example 14 can optionally be configured such that the at least one orthopedic device includes a plurality of different sized tibial broaches.

In Example 16, a method can comprise inserting a guide pin into an end of a natural or resection bone, such as a resected proximal end of a tibia; attaching a device to an orthopedic device holder, including inserting a locking member, of a body member of the orthopedic device holder, into a recess of the device; advancing the orthopedic device holder onto the guide pin, including advancing a distal end of the body member and a distal end of a cannulated plunger onto the guide pin; and releasing the device from the orthopedic device holder.

In Example 17, the method of Example 16 can optionally further comprise impacting a surface at a proximal end of the body member.

In Example 18, the method of any one or any combination of Examples 16 or 17 can optionally be configured such that attaching the device to the orthopedic device holder includes aligning a locating member, disposed on an opposite side of the body member distal end from the locking member, with a locating member disposed on the device.

In Example 19, the method of any one or any combination of Examples 16-18 can optionally be configured such that releasing the device from the orthopedic device holder includes moving the cannulated plunger from a second position, in which the plunger distal end extends past the body member distal end, toward a first position, in which the plunger distal end assumes a more proximal position.

In Example 20, the method of Example 19 can optionally be configured such that moving the cannulated plunger from the second position toward the first position includes urging a refraction handle, coupled to a plunger proximal end, against a resilient member force.

In Example 21, the method of any one or any combination of Examples 16-20 can optionally be configured such that attaching the device to the orthopedic device holder includes attaching a tibial broach to the orthopedic device holder.

In Example 22, the method of any one or any combination of Examples 16-20 can optionally be configured such that attaching the device to the orthopedic device holder includes attaching a provisional implant to the orthopedic device holder.

In Example 23, the orthopedic device holder, system, and method of any one or any combination of Examples 1-22 can optionally be configured such that all elements, operations, or other options recited are available to use or select from.

These and other examples and features of the present orthopedic device holder, system, and method will be set forth in part in the following Detailed Description. This Overview is intended to provide non-limiting examples of the present subject matter—it is not intended to provide an exclusive or exhaustive explanation. The Detailed Description below is included to provide further information about the present orthopedic device holder, system, and method.

BRIEF DESCRIPTION OF THE DRAWINGS

In the drawings, like numerals can be used to describe similar elements throughout the several views. Like numerals can be used to represent different views or configurations of similar elements. The drawings illustrate generally, by way of example, but not by way of limitation, various embodiments discussed in the present document.

DETAILED DESCRIPTION

In some surgical procedures, it can be important to be able to change modular tools or devices quickly, as in the case of a broaching system for creating a cavity in a bone. An orthopedic broach can form a uniquely shaped cavity and can be manipulated by moving the broach deeper into an area of bone to be formed. In order to increase a size of the cavity, it may be necessary to use a series of progressively larger broaches. In instances such as this, when a surgeon may need to change tools or devices quickly, an orthopedic device holder as disclosed herein can be helpful and important.

As part of the same surgical procedure, the surgeon can install one or more provisional implant prostheses. The provisional implant prostheses can aid in proper locating and sizing of a final implant prosthesis. The orthopedic device holder disclosed herein can be configured for use with a cutting tool, such as one or more broaches, as well as a fitting tool, such as a provisional implant prosthesis. During a surgical procedure, the surgeon may be required to attach a broach, then a fitting device, then another broach, etc. In the following Detailed Description, it is to be understood that the orthopedic device holder can be configured to operate with any suitable device for which such a quick connection/release would be beneficial, including broaching and provisional devices.

The present orthopedic device holder is configured to provide a quick and easy releasable connection for an orthopedic device. The device holder can include a lumen configured to receive a guide pin. The orthopedic device holder can have applications in difficult to reach locations where an orthopedic device needs connecting or releasing. The orthopedic device holder can also prove useful in miniature applications to provide a securable, releasable connection for small orthopedic devices. The orthopedic device holder and its components can be made of a wide variety of materials, such as metal alloys, stainless steels, aluminum, titanium, polymers, or carbon fiber.

Figure 1:
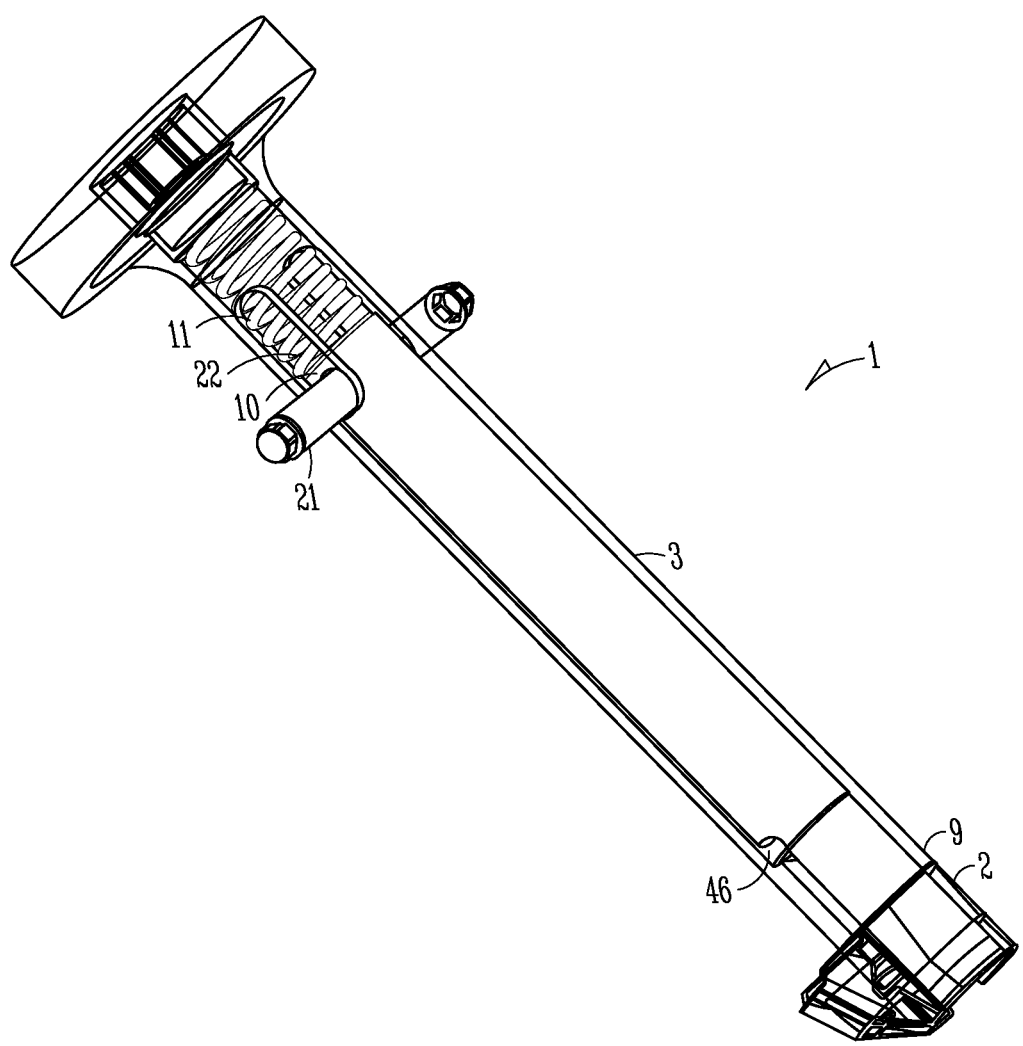
FIG. 1 illustrates an isometric view of an orthopedic device holder, as constructed in accordance with at least one embodiment.
Figure 2:
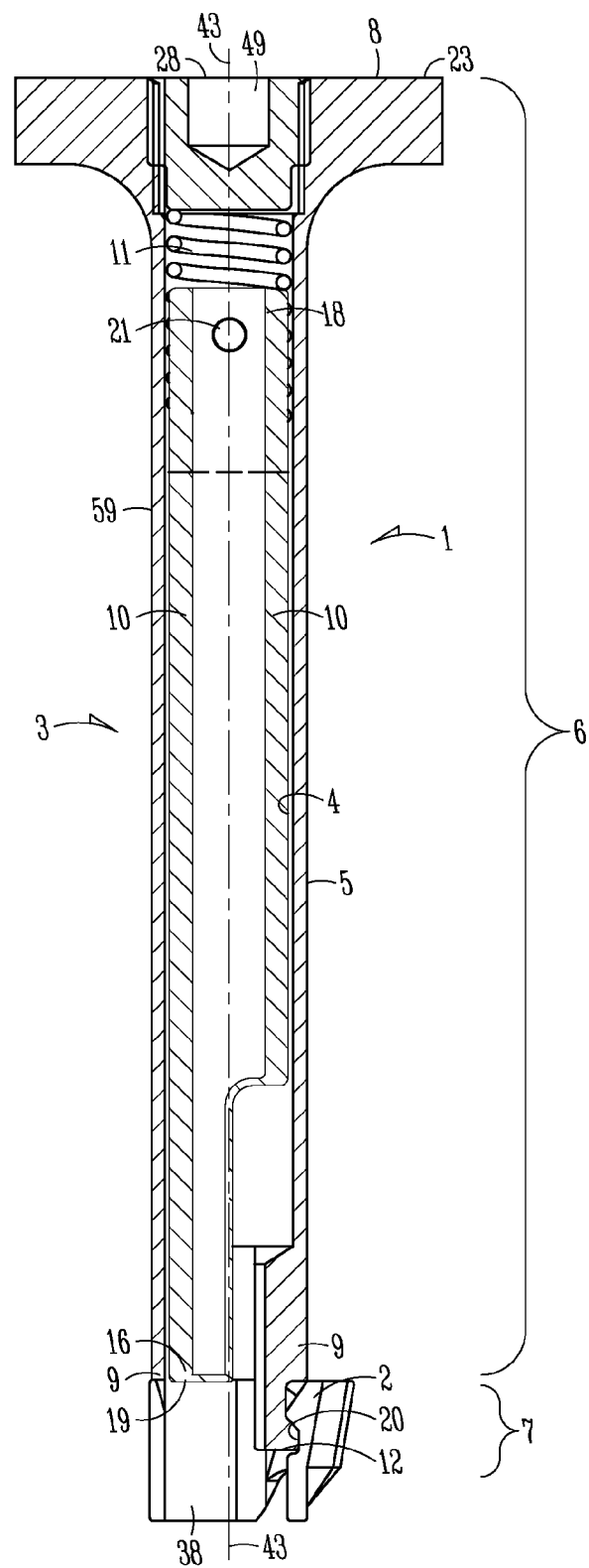
FIG. 2 illustrates a cross-section of an orthopedic device holder with a plunger in a first position, as constructed in accordance with at least one embodiment.

FIGS. 1-2 illustrates an orthopedic device holder 1 releasably connected to an orthopedic device 2. The device 2 can be clamped or otherwise secured to the device holder 1 by first inserting a locking member 12 into a locking member mating recess 20 of the device 2. A resilient member 11 can then be allowed to bias a plunger 10 into a plunger mating recess 38 of the device 2.

The device holder 1 can include a body member 3, which can serve as an outer structural framework 59 for the device holder 1. In FIG. 1, the body member 3 is illustrated in a partially transparent form to show internal structures of the device holder 1. In a cross section transverse to a longitudinal axis 43, the device holder 1 can include a round, oval, or rectangular shape. The body member 3 can be comprised of two sections, a longitudinal main body 6 and an extension portion 7. The extension portion 7 can extend distally beyond a main body distal end 9. The main body 6 can include an exterior surface 5 and an interior surface 4. A cannulated plunger 10 can be slidably mounted adjacent the interior surface 4. In this location, the plunger 10 can be moved from a second position 17 (see FIG. 3) to a first position 16 (as illustrated in FIG. 2). In the first position 16, the plunger distal end 19 can be retracted to a position near the main body distal end 9. A retraction handle 21 can be coupled to the plunger 10. In an example, a resilient member 11 is located at a plunger proximal end 18. The resilient member 11 can be a spring, an elastomeric member, a rubber bushing, a hydraulic device, or an air activated device. The resilient member 11 can bias the plunger 10 towards the second position 17. By applying force to the retraction handle 21, a surgeon can move the plunger 10 from the second position 17 towards the first position 16. A slot 22 in the body member 3, specifically the main body 6, can allow movement of the retraction handle 21. In an example, the plunger 10 can be moved between the first position 16 and the second position 17 and secured at either position without a resilient member.

At a proximal end of the resilient member 11, a retainer 28 can be coupled to the main body 6 by threading, press fitting, gluing, welding, brazing, or other manner. The retainer 28 can include a driving member 49, such as a hex socket or a receiver for a screw driver.

In an example, the device holder 1, can have an impaction surface 23 positioned at a main body proximal end 8. The impaction surface 23 can have a radial dimension, which is transverse to the longitudinal axis 43. The impaction surface 23 can have a larger cross-sectional area than a cross-sectional area of the main body distal end 9. The impaction surface 23 can be integral with or coupled to the main body 6. The impaction surface 23 can be configured to receive impact blows, such as hammer blows, used during a surgical procedure. The main body 6 can be configured to withstand the impact blows.

Figure 3:
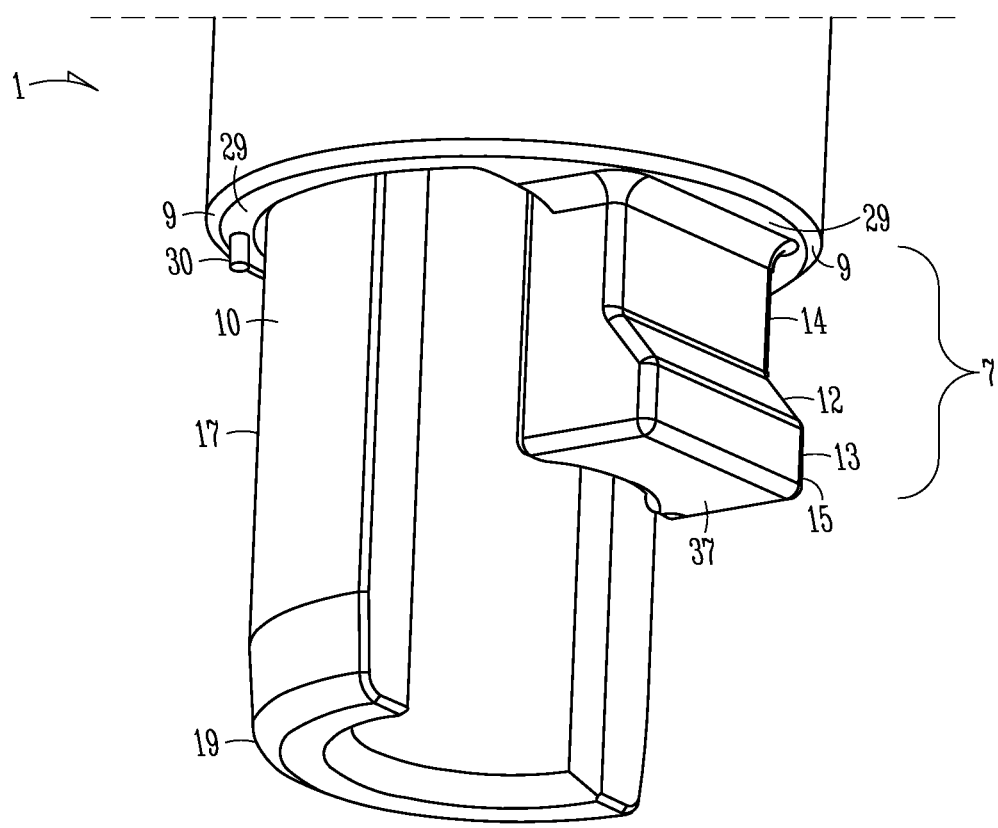
FIG. 3 illustrates an isometric view of a combination, including a locking member and a plunger in a second position, configured to securely hold an orthopedic device, as constructed in accordance with at least one embodiment.

FIG. 3 illustrates a close up of a distal end of the device holder 1. The plunger 10 is shown in the second position 17 and the plunger distal end 19 can be extended past the main body distal end 9. The extension portion 7 extends distally from the main body distal end 9. The extension portion 7 can include a locking member 12 and an arm member 14.

The locking member 12 can be shaped as a protrusion, a hook, a dovetail, or a pin. In the illustrated example, the locking member 12 includes a semi-circular dovetail 37 shape. The locking member 12 could have a variety of shapes and sizes, depending on the use of the device holder 1. For example, if the device 2 is a broach and impacting is involved, the dimensions of the locking member 12 and the extension portion 7 can be configured strong enough to resist breakage. The device holder 1 can be used to extract a device 2 and in such an application, where a pulling force is desirable, the locking member 12 can include a more hook-like form. A locking member 12 including a hook-like form can be inserted into a locking member mating recess 20 (see FIG. 4) in a twisting manner instead of inserting in a straight forward motion. The locking member 12 can have a first outer radial size 13 that extends farther out radially than a second outer radial size of the arm member 14.

An engagement surface 29 can be positioned at the main body distal end 9 and can be substantially transverse to the longitudinal axis 43 (see FIG. 2) of the device holder 1. A holder locating member 30 can be disposed on the main body distal end 9. The holder locating member 30 can be a spring-loaded ball, a protrusion, a cavity, a slot, a pin, or a key formed to position a side of the device holder 1, which is substantially opposite the locking member 12, onto a corresponding device locating member 39 (see FIG. 4) prior to releasing the plunger 10 into a plunger mating recess 38 (see FIG. 4).

Figure 4:
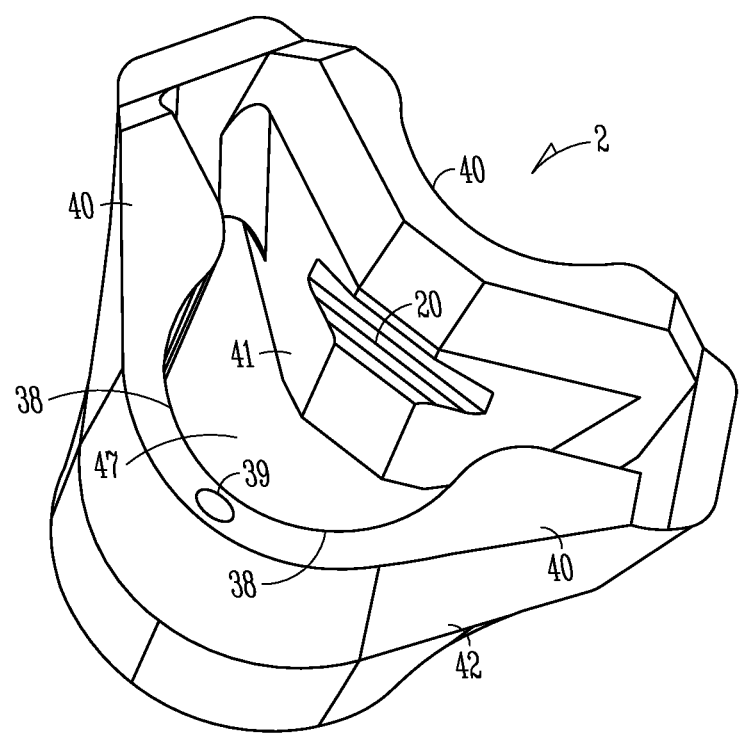
FIG. 4 illustrates an isometric view of an orthopedic broach, as constructed in accordance with at least one embodiment.

FIG. 4 illustrates an orthopedic device 2 in the form of a broach. The device 2 can have a device interior surface 41 and a device exterior surface 42. A locking member mating recess 20 can be located on the device interior surface 41 and can have a shape corresponding to a shape of the locking member 12 (see FIG. 3). The device 2 can include a plunger mating recess 38 substantially opposite the locking member mating recess 20. The plunger mating recess 38 can be shaped to correspond to outer dimensions of the plunger 10, particularly the plunger distal end 19 (see FIG. 3). A device locating member 39 can be disposed near a device engagement surface 40 and can include a spring-loaded ball, a protrusion, a cavity, a slot, a pin or a key shaped and positioned to correspond to the holder locating member 30 (see FIG. 3).

Referring to FIGS. 3 and 4, operation of the device holder 1 can be as follows. With the plunger 10 retracted to a first position 16 (see FIG. 2), the locking member 12 of the device holder 1 can be inserted into the locking member mating recess 20 of the device 2. In this position, the device 2 can be engaged with the device holder 1, but is not yet secured to it. In an example, the holder locating member 30 can be engaged with the device locating member 39. The retraction handle 21 (see FIG. 1) can then be released and the plunger 10 can extend past the main body distal end 9 and into the plunger mating recess 38. The plunger distal end 19 can be rounded or beveled to aid in the entry of the plunger 10 into the plunger mating recess 38. In an example, the holder locating member 30 and the device locating member 39 are not present and the plunger distal end 19 self-locates into the plunger mating recess 38, aided by a beveled or rounded plunger distal end 19. The engagement surface 29 positioned at the main body distal end 9 should now abut the device engagement surface 40 and the combination of the locking member 12 and the plunger 10 in the second position 17 secures the device 2 to the device holder 1.

In an example, the device 2 can be a broach that is impacted into a bone. The plunger engagement surface 29 and the device engagement surface 40 can be configured to withstand and transmit impacting blows from the device holder 1 to the device 2. In an example, the extension portion 7 and the locking member 12 can be configured to fit into a device mating recess 20 located on the device external surface 42, instead of the device interior surface 41. A surgeon can have a series of broaches of various sizes and shapes in an orthopedic system. These broaches can correspond to the shapes of implantable surgical devices.

Figure 5:
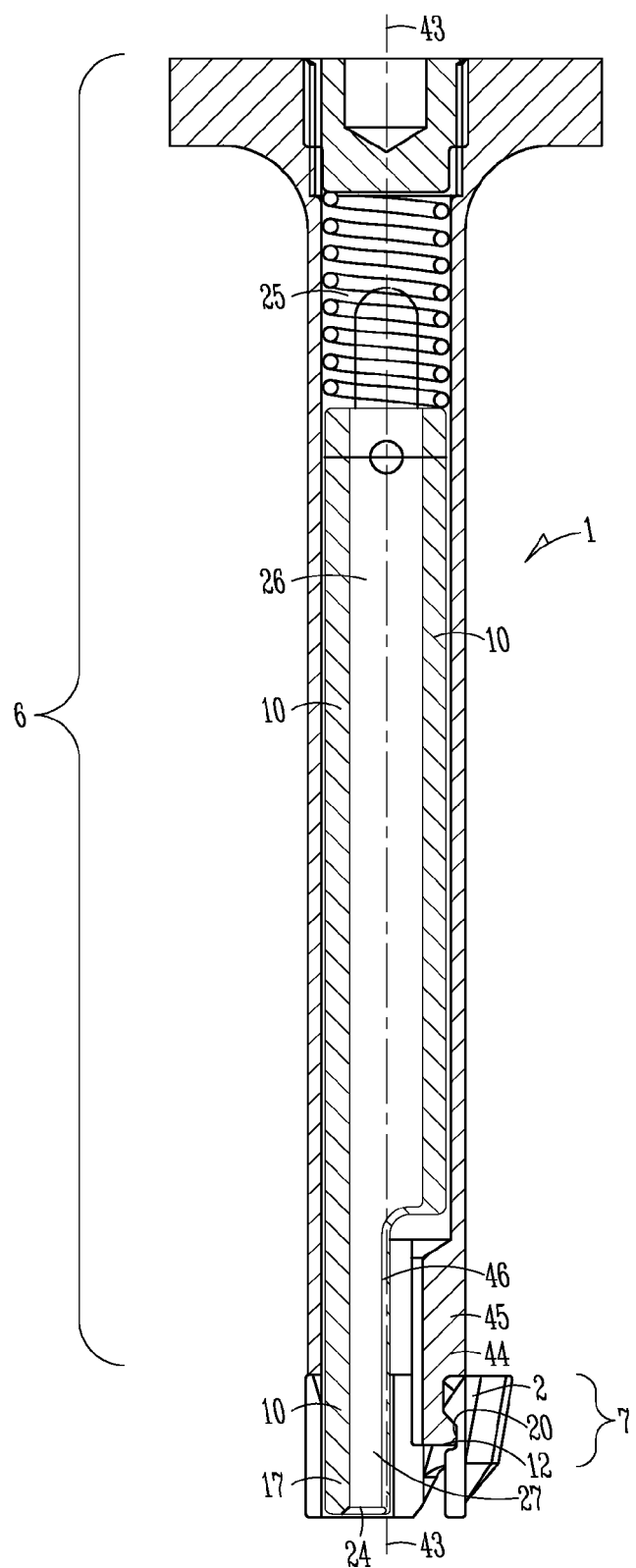
FIG. 5 illustrates a cross-section of an orthopedic device holder with a plunger in a second position, as constructed in accordance with at least one embodiment.
Figure 6:
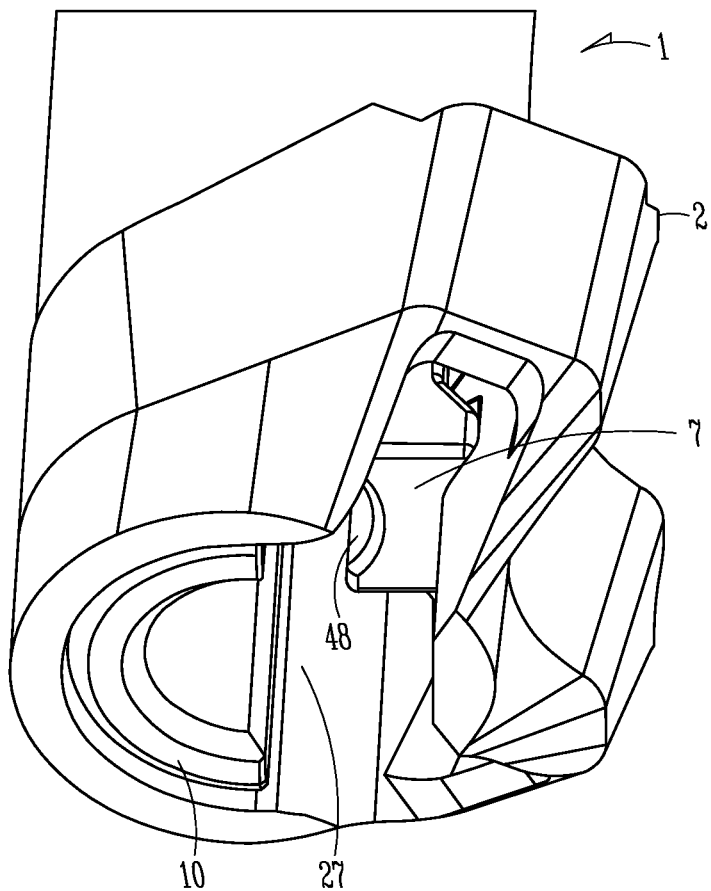
FIG. 6 illustrates a close up isometric view of a connection between a distal end of an orthopedic device holder and an orthopedic broach, as constructed in accordance with at least one embodiment.

FIGS. 5-6 illustrate the device holder 1 securely connected to the device 2. The plunger 10, now in the second position 17, can extend past the main body distal end 9 into the plunger mating recess 38 of the device 2. From a distal viewpoint, the secure connection can be seen in the close up view of FIG. 6.

In some surgical applications, a guide pin can be used during a locating procedure. The device holder 1 can have a lumen 24 that extends the length of a longitudinal axis 43 of the device holder 1. The lumen 24 can be divided into three sections: a first portion 25, a second portion 26, and a third portion 27. The first portion 25 can be formed by an interior surface of the main body 6 proximal end. The second portion 26 of the lumen 24 can be formed by an interior surface of the plunger 10. The third portion 27 can be formed, in part, by a curved interior surface 48 of the extension portion 7. The third portion 27 is illustrated in FIG. 6 and can include a part of an indentation 46 portion of the plunger 10 as well as the curved interior surface 48. The device 2 can also include a device lumen 47 (see FIG. 4). In operation, the device 2 is connected to the device holder 1, and the assembly, including the device 2 and the device holder 1, can be installed over a locating guide pin. In some example applications, a guide pin is not used and, as such, the device holder 1 need not be cannulated. In such examples, the plunger 10 can be solid or without a lumen 24.

In an example, the locking member 12 (see FIG. 3) of the extension portion 7 can include an outward radial dimension no greater than the outward radial dimension of the main body 6. In an example, a main body lower portion 44 can have a thickened cross section 45 to add strength to the extension portion 7. In order to avoid contact with the thickened cross section 45 during movement from the first position 16 (see FIG. 2) to the second position 17, the plunger 10 can have an indentation 46 (see also, FIG. 1). In an example, the outward radial dimension of the extension portion 7, or a portion thereof, can be greater than the outward radial dimension of the main body 6 and the plunger 10 can be configured as a straight tube without an indentation.

Figure 7:
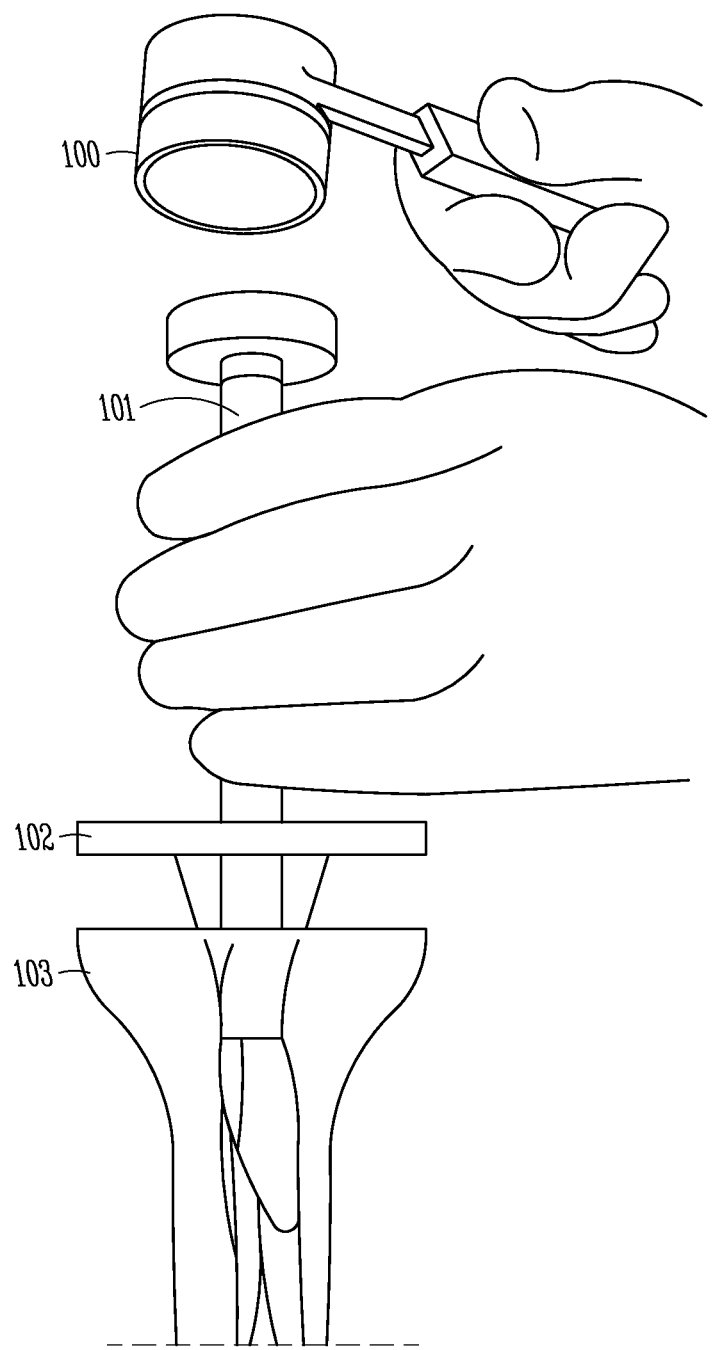
FIG. 7 illustrates a schematic view of an installation of a provisional implant using an orthopedic device holder.

FIG. 7 illustrates an installation of a provisional implant 102 into a tibia 103. An orthopedic device holder 101 can be attached to the provisional implant 102 using the elements described above, and in reference to FIGS. 1-6. A hammer 100 can be used to install the provisional implant 102 into a bone, such as a tibia 103.

Figure 8:
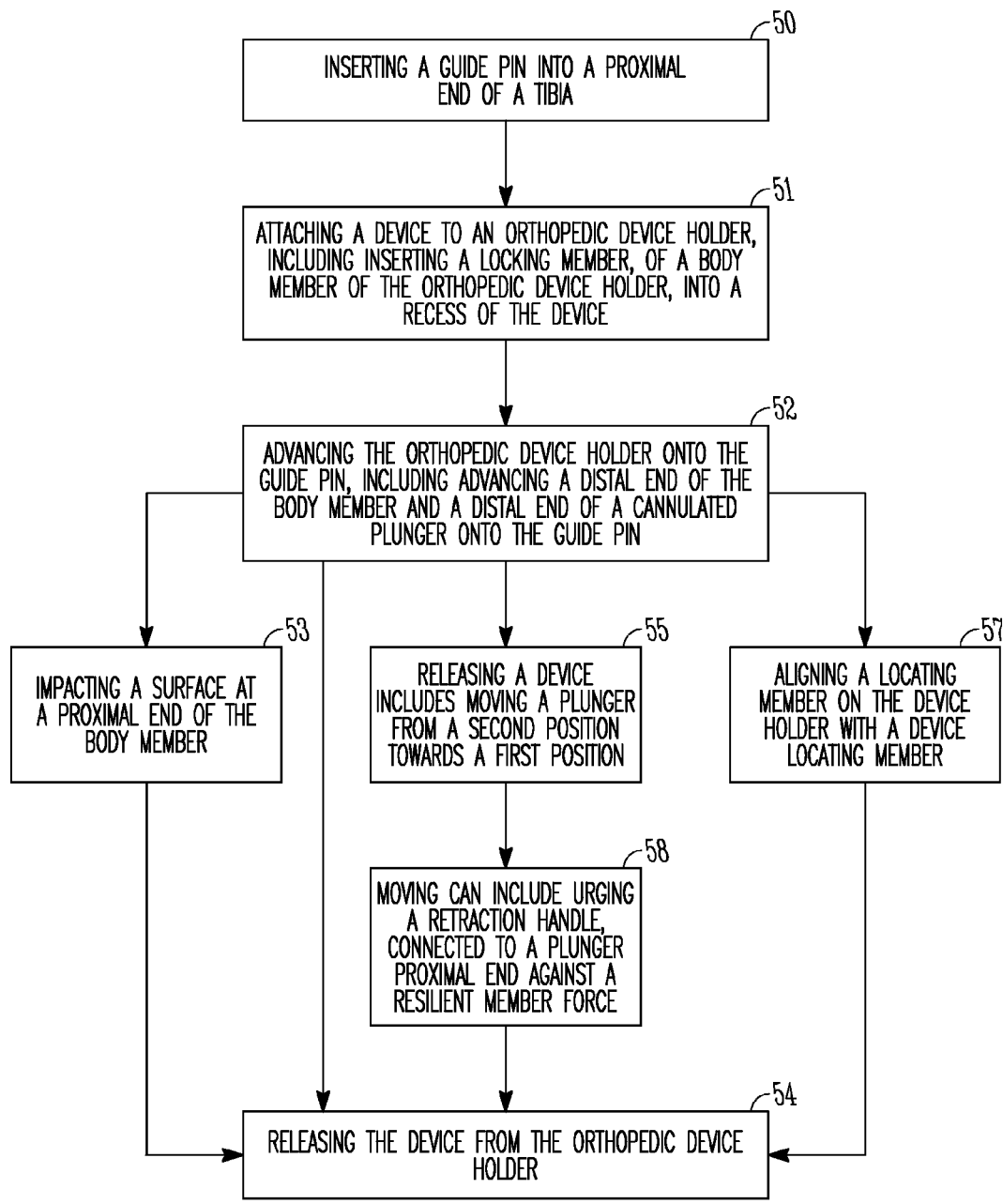
FIG. 8 illustrates an example method of using an orthopedic device holder.

FIG. 8 illustrates and example method of using the present orthopedic device holder. The Detailed Description associated with FIGS. 1-6 can also be used to describe and understand the components of the method. The method can be conducted in a series of steps. At step 50, a guide pin can be inserted into a proximal end of a tibia. A location of the guide pin can be checked or verified using radiographic or fluoroscopic methods. The guide pin can provide an accurate base location for a surgical procedure. At step 51, a tibial broach can be attached to the orthopedic device holder. This step can include inserting the locking member of the body member of the device holder into the locking member mating recess of the orthopedic broach. An example can include the device holder 1 and the device 2 of FIG. 1. FIGS. 3 and 4 illustrate an example of the locking member 12 and the locking member mating recess 20 of a tibial broach. FIG. 2 illustrates the locking member 12 as a portion of the body member 3 and further illustrates the engagement of the locking member 12 with the locking member mating recess 20.

Returning to FIG. 8, at step 52, the device holder can be advanced onto the guide pin. This step can include advancing the distal end of the body member and the distal end of the cannulated plunger onto the guide pin. FIG. 5 illustrates the plunger 10 connected to the broach 2. The surgeon can place the lumen 24 of the device holder/device assembly over the guide pin and advance the assembly to a bone surface.

The method can subsequently take one of several pathways, including:
1) At step 54, the broach is released from the device holder;
2) At step 53, a surface at the proximal end of the body member is impacted, such as through the use of a hammer, to drive the broach deeper into a bone, thereby forming a bone cavity;
3) At step 55, the broach can be released from the device holder through movement of the plunger from the second position to the first position. This movement can include, at step 58, using the retraction handle, coupled to the plunger proximal end, against a resilient member force;
4) At step 57, the locating member on the device holder can be aligned with the device locating member.

Steps 53, 55, 57, and 58 can be followed by step 54. At step 54, the broach can be released and another broach, having a differing size or shape, can optionally be connected to the device holder. A broach is a specialized toothed cutting tool that can have a series of teeth at increasingly greater tooth height. An example of bone cutting with a broach is to use an impact tool, such as a manual hammer or pneumatic hammer, to force the broach deeper into the bone. An example of step 53 can be conceptualized in association with FIG. 2. The device holder 1 has the impacting surface 23 on the proximal end of the body member 3. This impacting surface 23 can be hit with a hammer to drive the broach 2 into a bone.

Step 55 includes moving the plunger from the second position to the first position. FIG. 5 illustrates an example of the plunger 10 in the second position 17. The locking member 12 is inserted into a locking member mating recess 20 and the plunger is in the second position 17, such that the broach 2 is securely mounted on the device holder 1. After moving the plunger 10 to a first position 16, as illustrated in FIG. 2, the broach 2 will no longer be secured to the device holder 1 and can be released.

Step 58 follows step 55. Movement of the plunger 10 can include urging the retraction handle, coupled to the plunger proximal end, against the resilient member force. An example of these elements can be seen in FIG. 1. In order to move the plunger 10 from the second position 17 (see FIG. 5) to the first position 16 (see FIG. 2), the force of the resilient member 11 must be overcome.

Step 57 includes aligning the locating member 30 on the device holder 1 with a device locating member 39. An example of this alignment is illustrated in FIGS. 3 and 4. The device holder locating member 30 can be disposed near the engagement surface 29 at the main body distal end 9. The locating member 30 can take many forms, such as a protrusion, a cavity, a slot, a pin, or a key. Before the plunger 10 is extended from the first position 16 (see FIG. 2) to the second position 17, it can be advantageous to align the device holder 1 to the broach 2. After the locking member 12 has been inserted into the locking member mating cavity 20 of the broach 2, some rotational movement between the device holder 1 and the broach 2 can still be present. By shifting the device holder 1 slightly side to side, on a side opposite from the locking member 12, the device holder locating member 30 can become engaged with the device locating member 39. The plunger mating recess 38 of the broach 2 can be aligned with the plunger distal end 19 and the plunger 10 can be released to the second position 17.

Although the method has been described is association with a tibial broach, similar method steps can be used at other locations in a patient's body. One or more of the general steps can be followed using other tools or devices, such as a rasp.

The above Detailed Description includes references to the accompanying drawings, which form a part of the Detailed Description. The drawings show, by way of illustration, specific embodiments in which the present catheter orthopedic device holder, system, and method can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" are used to refer to an amount that is nearly, almost, or in the vicinity of being equal to a stated amount. In this document, the terms "proximal" and "distal" are used to refer to a device holder element location relative to a caregiver user. For example, a proximal element portion is a portion closer to the user of the device holder, whereas a distal element portion is a portion farther away from the user of the device holder, such as the portions interacting with a patient recipient. In this document, the term "patient" is intended to include mammals, such as for human applications or veterinary applications.

In the appended claims, the terms "including" and "in which" are used as the plain-English equivalents of the respective terms "comprising" and "wherein." Also, in the following claims, the terms "including" and "comprising" are open-ended, that is, an assembly, system, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. An orthopedic device holder configured to hold and release an orthopedic device, comprising:
   a body member including a longitudinal main body extending from a main body proximal end to a main body distal end and including an interior surface and an exterior surface, and an extension portion projecting distally from the main body distal end and including a locking member;
   a cannulated plunger, extending from a plunger proximal end to a plunger distal end, slidably mounted adjacent the interior surface and movable between a first position and a second position, the plunger configured such that, in the second position, the plunger distal end extends past the main body distal end and, in the first position, the plunger distal end assumes a more proximal position; and
   a resilient member, positioned adjacent the plunger proximal end, configured to urge the plunger towards the second position,
   wherein when the plunger is in the second position, the orthopedic device is contacted by and held by the plunger distal end and the locking member, and when the plunger is in the first position, the plunger is no longer in contact with the orthopedic device thereby releasing the orthopedic device from the holder.

2. The device holder of claim 1, wherein the locking member is configured to fit into a mating recess of an orthopedic device.

3. The device holder of claim 1, wherein the locking member has a first outer radial size and the extension portion further comprises an arm member having a second outer radial size that is less than the first outer radial size.

4. The device holder of claim 2, wherein at least a portion of the main body distal end includes an engagement surface substantially perpendicular to a longitudinal axis of the device holder.

5. The device holder of claim 4, wherein the engagement surface comprises a locating member, disposed on an opposite side of the main body distal end from the extension portion, configured to mate with a corresponding locating member disposed on the orthopedic device.

6. The device holder of claim 1, further comprising a retraction handle, coupled to the plunger proximal end, configured to move the plunger from the second position toward the first position.

7. The device holder of claim 6, wherein the longitudinal main body includes one or more slots configured to guide movement of the retraction handle between a second position, associated with the second position of the plunger, and a first position, associated with the first position of the plunger.

8. The device holder of claim 1, wherein the main body proximal end includes an impaction surface having a larger cross-sectional area than a cross-sectional area of the main body distal end.

9. The device holder of claim 8, further comprising a resilient member retainer coupled to a lumen within the main body proximal end.

10. The device holder of claim 1, wherein the body member and the cannulated plunger are configured to collectively define a lumen extending from the main body proximal end, through the cannulated plunger, and through the main body distal end.

11. The device holder of claim 10, wherein a first portion of the lumen is formed by an interior surface of the main body proximal end, a second portion of the lumen is formed by an interior surface of the plunger, and a third portion of the lumen is formed, in part, by an interior surface of the extension portion.

12. The device holder of claim 1, wherein the first outer radial size of the locking member is substantially equal to an outer radial size of the longitudinal main body.

13. The device holder as in claim 1, wherein the locking member includes a semi-circular dovetail configuration.

14. An orthopedic system, comprising:
   the orthopedic device holder of claim 1; and
   at least one orthopedic device including a recess sized and shaped to receive a portion of the locking member.

15. The orthopedic system of claim 14, wherein the at least one orthopedic device includes a plurality of different sized tibial broaches.

\* \* \* \* \*